United States Patent [19]
Inazu et al.

[11] Patent Number: 6,100,280
[45] Date of Patent: Aug. 8, 2000

[54] NARCOTIC ANTAGONIST

[75] Inventors: Masato Inazu; Mariko Harada; Tomoko Masuda, all of Yokohama, Japan

[73] Assignee: Pola Chemical Industries, Inc., Shizuoka, Japan

[21] Appl. No.: 09/085,463

[22] Filed: May 28, 1998

Related U.S. Application Data

[63] Continuation of application No. 08/676,627, Jul. 10, 1996, abandoned.

[30] Foreign Application Priority Data

Jul. 11, 1995 [JP] Japan .................................. 7-174566

[51] Int. Cl.$^7$ .................................................. A61K 31/495
[52] U.S. Cl. ............................................ 514/340; 514/255
[58] Field of Search .............................................. 514/255

[56] References Cited

FOREIGN PATENT DOCUMENTS

| 0 612 738 A1 | 8/1994 | European Pat. Off. . |
| 0 706 796 A1 | 4/1996 | European Pat. Off. . |
| 1 497 083 | 1/1978 | United Kingdom . |
| PCT/WO 92/16211 | 10/1992 | WIPO . |
| PCT/WO 95/00149 | 5/1995 | WIPO . |

OTHER PUBLICATIONS

Database WPI Week 9519, Derwent Publications Ltd., London, Great Britain; AN 95–144708, XP 002045048 (Abstract of JP 07069892A).
Database WPI Week 9519, Derwent Publications Ltd., Lond, Great Britain; AN 95–144707, XP 002045049 (Abstract of JP 07069891A).

*Primary Examiner*—Keith D. MacMillan
*Attorney, Agent, or Firm*—Bacon & Thomas

[57] ABSTRACT

A narcotic antagonist comprising, as its active component, a compound represented by the following formula (1) or a physiologically acceptable salt thereof:

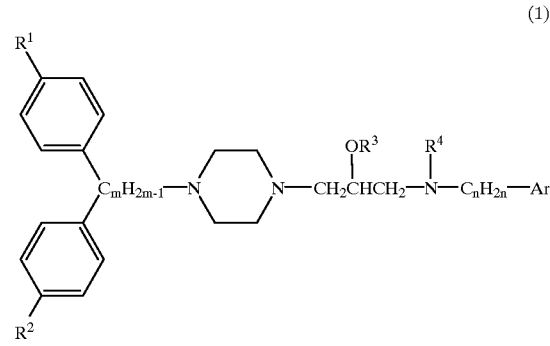

(1)

wherein each of $R^1$ and $R^2$, which may be identical to or different from each other, represents a hydrogen atom or a halogen atom; $R^3$ represents a hydrogen atom, an alkyl group, or an acyl group; $R^4$ represents a hydrogen atom, an alkyl group, an acyl group, an alkylsulfonyl group, or a carboxyl group which may be esterified; Ar represents a phenyl group which may have 1 to 3 substituents selected from the group consisting of a halogen atom, an alkyl group, an alkoxyl group, a nitro group, an amino group, an alkylamino group, and a hydroxyl group or Ar represents a monocyclic aromatic heterocyclic ring having a nitrogen atom; m represents a number of 1 to 5 inclusive; and n represents a number of 0 to 5 inclusive. Also, a medicament for the prevention and treatment of narcotic dependence is provided. The medicament is effective in the prevention and treatment of narcosic dependence due to cocaine, etc.

13 Claims, No Drawings

NARCOTIC ANTAGONIST

This application is a continuation of Ser. No. 08/676,627, filed Jul. 10, 1996, abandoned, which claims priority to Japan 174566/1995, filed Jul. 11, 1995.

BACKGROUND OF THE INVENTION

1. Field of the Invention

The present invention relates to a narcotic antagonist and a medicament for the prevention and treatment of narcotic dependence.

2. Background Art

Narcotics, typically represented by cocaine, have rapidly spread worldwide since the Vietnam War. Because narcotics cause strong dependency, once a user becomes dependent on them, it is difficult for the user to abandon his habitual use of them. Thus, despite great efforts made in many countries for controlling narcotics, any attempts so far have been unsuccessful, and permitted them to further spread worldwide.

Under the above circumstances, various attempts have been made to develop compounds for treating cocaine dependence. For example, certain piperazine derivatives which act on neuroreceptors have been found to have a therapeutic action for narcotic dependence (International Patent Publication (kohyo) No. 4-504859). However, when such a piperazine derivative is used at a concentration high enough to cure narcotic dependence, it often happens that the derivative also strongly exhibits other activities, giving adverse side effects. Therefore, substances that strongly act on narcotic receptors are still desired.

In view of the foregoing, the present inventors carried out extensive screenings using narcotic antagonism as an index and found that the compounds represented by the following formula (1) described below possess strong narcotic antagonism and thus are useful as preventive and therapeutic agents for narcotic dependence. The present invention was accomplished based on this finding.

SUMMARY OF THE INVENTION

Accordingly, an object of the present invention is to provide a narcotic antagonist comprising, as its active component, a compound represented by the following formula (1) or a physiologically acceptable salt thereof:

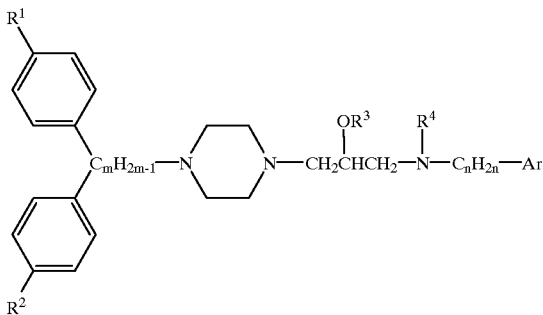

(1)

wherein each of $R^1$ and $R^2$, which may be identical to or different from each other, represents a hydrogen atom or a halogen atom; $R^3$ represents a hydrogen atom, an alkyl group, or an acyl group; $R^4$ represents a hydrogen atom, an alkyl group, an acyl group, an alkylsulfonyl group, or a carboxyl group which may be esterified; Ar represents a phenyl group which may have 1 to 3 substituents selected from the group consisting of a halogen atom, an alkyl group, an alkoxyl group, a nitro group, an amino group, an alkylamino group, and a hydroxyl group or Ar represents a monocyclic aromatic heterocyclic ring having a nitrogen atom; m represents a number of 1 to 5 inclusive; and n represents a number of 0 to 5 inclusive.

Another object of the present invention is to provide a preventive/therapeutic agent for narcotic dependence comprising, as its active component, a compound represented by the above formula (1) or a physiologically acceptable salt thereof.

A further object of the present invention is to provide use of a compound represented by the following formula (1) or a physiologically acceptable salt thereof in the manufacture of a narcotic antagonist or a medicament for the prevention and treatment of narcotic dependence.

A still further object of the present invention is to provide a method for preventing or treating narcotic dependence comprising the administration of an effective amount of a compound represented by the above formula (1) or a physiologically acceptable salt thereof.

DESCRIPTION OF PREFERRED EMBODIMENTS

The compounds represented by the above formula (1) are known per se. They are also known to have calcium antagonism, dopamine reuptake inhibiting action, serotonin reuptake inhibiting action, and anti-oxidization action (WO92/05165). However, their strong narcotic antagonism was never known until reported by the present invention.

In compounds represented by formula (1) which are used in the present invention, each of $R^1$ and $R^2$ is a hydrogen atom or a halogen atom. Examples of halogen atoms include a fluorine atom, a chlorine atom, and an iodine atom.

As described hereinabove, $R^3$ represents a hydrogen atom, an alkyl group, or an acyl group. Preferred alkyl groups are C1–C6 linear or branched alkyl groups. Illustrative examples thereof include methyl, ethyl, n-propyl, isopropyl, n-butyl, isobutyl, sec-butyl, and tert-butyl. Examples of acyl groups include C1–C6 alkanoyl groups, of which formyl, acetyl, propionyl, and butyryl are particularly preferred.

As described hereinabove, $R^4$ represents a hydrogen atom, an alkyl group, an acyl group, an alkylsulfonyl group, or a carboxyl group which may be esterified. As examples of alkyl groups and acyl groups, the groups listed for $R^3$ are mentioned. Useful alkylsulfonyl groups may have 1–6 carbon atoms. Specific examples thereof include methylsulfonyl, ethylsulfonyl, propylsulfonyl, and isopropylsulfonyl. The carboxyl groups which may be esterified may be carboxyl or C1–C6 alkoxycarbonyl. Examples of C1–C6 alkoxycarbonyl groups include methoxycarbonyl, ethoxycarbonyl, and isopropoxycarbonyl.

As described hereinabove, Ar represents a phenyl group which may have 1 to 3 substituents selected from the group consisting of a halogen atom, an alkyl group, an alkoxyl group, a nitro group, an amino group, an alkylamino group, and a hydroxyl group or Ar represents a monocyclic aromatic heterocyclic ring having a nitrogen atom. As examples of a halogen atom which may be substituted by a phenyl group, those listed for $R^1$ are mentioned. As the alkyl group, those listed for $R^3$ may be used. Examples of alkoxyl groups include C1–C6 alkoxyl, of which methoxy, ethoxy, n-propoxy, and isopropoxy are more preferred. Useful alkylamino groups may have 1–6 carbon atoms. Particularly, methylamino, ethylamino, n-propylamino, and isopropylamino are preferred. Examples of the monocyclic aromatic heterocyclic ring having a nitrogen atom include pyridyl and pyrimidyl. Pyridyl is particularly preferred.

The numbers m and n are preferably in the ranges of 1–5, and 0–4, respectively.

The compounds of the present invention which are represented by formula (1) may be prepared, for example, by the method described in WO92/05165.

Properties of formula (1) compounds differ depending on the species and numbers of their substituents. They are usually colorless to pale yellow liquids, amorphous, or solids. They are slightly soluble in water and are soluble in organic solvents such as methanol, chloroform, or benzene. Compounds of formula (1) can be readily purified by routine methods such as column chromatography or recrystallization.

Compounds of formula (1) may be converted into salts when they are mixed with acids. Acids usable for this purpose are not particularly limited so long as the resultant salts are physiologically acceptable. Examples of usable acids include mineral acids such as hydrochloric acid, phosphoric acid, sulfuric acid; and organic acids such as citric acid, oxalic acid, acetic acid, fumaric acid, maleic acid, maronic acid, and methanesulfonic acid. Of the listed acids, maleic acid is particularly preferred from the viewpoints of easy handling, low cost, and good chemical properties.

The thus-formed salts of formula (1) compounds are generally white, pale yellow, or pale blue solids. They have improved water solubility and stability relative to formula (1) compounds themselves.

Illustrative examples of the compounds represented by formula (1) which are used in the present invention include compounds 1 through 25 shown in Tables 1 through 5 below.

TABLE 1

| PR-No. | Structure | m | n | $R_1$ | $R_2$ | $R_3$ | $R_4$ | Compound Name |
|---|---|---|---|---|---|---|---|---|
| Cpd. 1 | 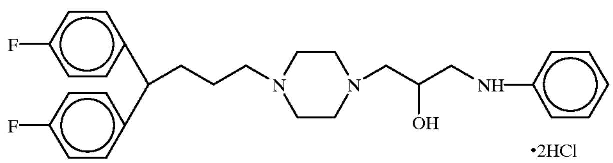 | 4 | 0 | F | F | H | H | 1-[4,4-bis(4-fluorophenyl)-butyl]-4-(2-hydroxy-3-phenylaminopropyl)piperazine.2HCl |
| Cpd. 2 | 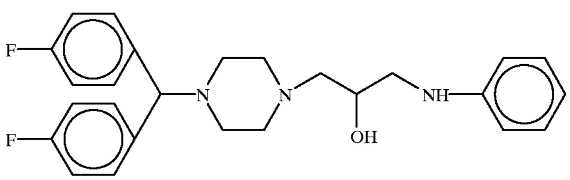 | 1 | 0 | F | F | H | H | 1-[bis(4-fluorophenyl)-methyl]-4-[2-hydroxy-3-phenylaminopropyl)-piperazine.2HCl |
| Cpd. 3 | 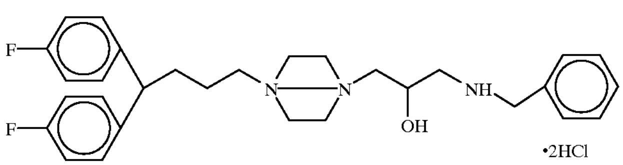 | 4 | 1 | F | F | H | H | 1-[4,4-bis(4-fluorophenyl)-butyl]-4-(2-hydroxy-3-benzylaminopropyl)-piperazine.2HCl |
| Cpd. 4 | 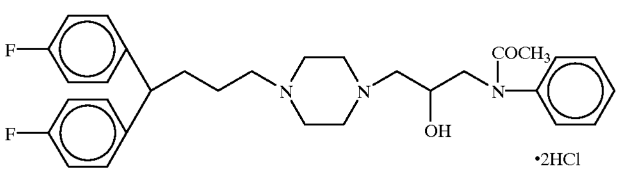 | 4 | 0 | F | F | H | $COCH_3$ | 1-[3-(N-(acetyl-N-phenyl-amino)-2-hydroxypropyl]-4-[4,4-bis(4-fluorophenyl)-butyl]piperazine.2HCl |
| Cpd. 5 | 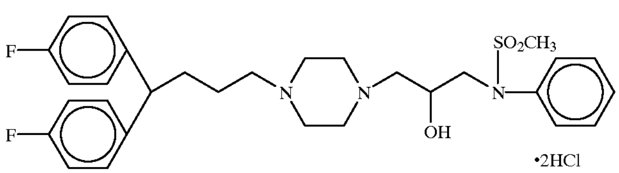 | 4 | 0 | F | F | H | $SO_2CH_3$ | 1-[4,4-bis(4-fluorophenyl)-butyl]-4-[2-hydroxy-3-(N-methylsulfonyl-N-phenylamino)propyl]piperazine.2HCl |

TABLE 2

| PR-No. | Structure | m | n | R₁ | R₂ | R₃ | R₄ | Compound Name |
|---|---|---|---|---|---|---|---|---|
| Cpd. 6 | [structure] | 4 | 0 | F | F | H | $CH_3$ | 1-[4,4-bis(4-fluoro-phenyl)-butyl]-4-[2-hydroxy-3-(N-methyl-N-phenyl-amino)-propyl]pi-perazine.$2C_4H_4O_4$ |
| Cpd. 7 | [structure] | 4 | 0 | F | F | $COCH_3$ | H | 1-(2-acetoxy-3-phenyl-amino-propyl)-4-[4,4-bis(4-fluoro-phenyl)butyl]pi-perazine.$2C_4H_4O_4$ |
| Cpd. 8 | [structure] | 4 | 0 | F | F | $CH_3$ | H | 1-[4,4-bis(4-fluoro-phenyl)-butyl]-4-(2-methoxy-3-phenylaminopropyl)pi-perazine.2HCl |
| Cpd. 9 | [structure] | 4 | 0 | F | F | H | H | 1-[4,4-bis(4-fluoro-phenyl)-butyl]-4-[3-(4-fluorophenyl-amino)-2-hydroxy-propyl]-pipera-zine.2HCl |
| Cpd. 10 | [structure] | 4 | 0 | F | F | H | H | 1-[4,4-bis(4-fluoro-phenyl)-butyl]-4-[3-(4-chlorophenyl-amino)-2-hydroxy-propyl]-pipera-zine.2HCl |

TABLE 3

| PR-No. | Structure | m | n | R₁ | R₂ | R₃ | R₄ | Compound Name |
|---|---|---|---|---|---|---|---|---|
| Cpd. 11 | [structure] | 4 | 0 | F | F | H | H | 1-[4,4-bis(4-fluorophenyl)-butyl]-4-[2-hydroxy-3-(3,4,5-trimethoxyphenylamino)-propyl]piperazine.$2C_4H_4O_4$ |
| Cpd. 12 | [structure] | 4 | 0 | F | F | H | H | 1-[4,4-bis(4-fluorophenyl)-butyl]-4-[3-(3,4-dychloro-phenylamino)-2-hydroxy-propyl]piperazine.2HCl |

TABLE 3-continued

| PR-No. | Structure | m | n | R₁ | R₂ | R₃ | R₄ | Compound Name |
|---|---|---|---|---|---|---|---|---|
| Cpd. 13 | 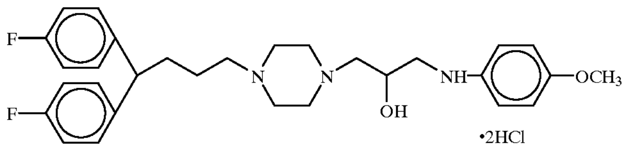 | 4 | 0 | F | F | H | H | 1-[4,4-bis(4-fluorophenyl)-butyl]-4-[2-hydroxy-3-(4-methoxyphenylamino)propyl]-piperazine.2HCl |
| Cpd. 14 | 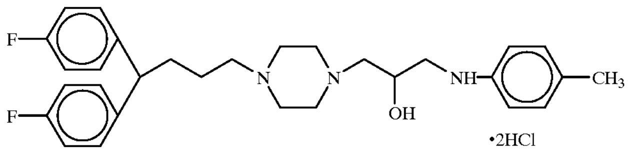 | 4 | 0 | F | F | H | H | 1-[4,4-bis(4-fluorophenyl)-butyl]-4-[2-hydroxy-3-(4-methylphenylamino)propyl]-piperazine.2HCl |
| Cpd. 15 | 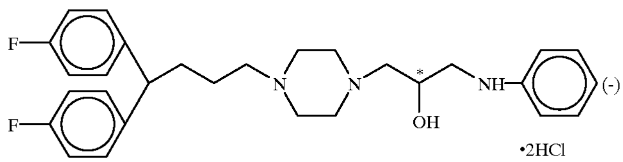 | 4 | 0 | F | F | H | H | (—)-1-[4,4-bis(4-fluorophenyl)butyl]-4-(2-hydroxy-3-phenylaminopropyl)-piperazine.2HCl |

TABLE 4

| PR-No. | Structure | m | n | R₁ | R₂ | R₃ | R₄ | Compound Name |
|---|---|---|---|---|---|---|---|---|
| Cpd. 16 | 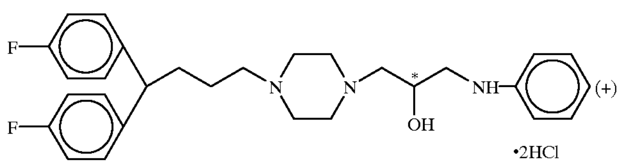 | 4 | 0 | F | F | H | H | (+)-1-[4,4-bis(4-fluorophenyl)butyl]-4-(2-hydroxy-3-phenylaminopropyl)-piperazine.2HCl |
| Cpd. 17 | 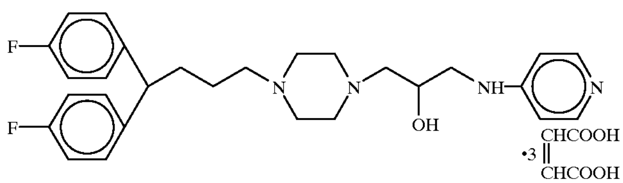 | 4 | 0 | F | F | H | H | 1-[4,4-bis(4-fluorophenyl)-butyl]-4-[2-hydroxy-3-(4-pyridylamino)propyl]-piperazine.2C₄H₄O₄ |
| Cpd. 18 | 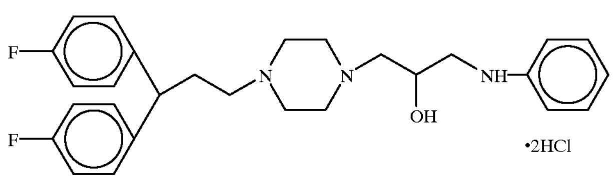 | 3 | 0 | F | F | H | H | 1-[3,3-bis(4-fluorophenyl)-propyl]-4-[2-hydroxy-3-phenylaminopropyl)piperazine |
| Cpd. 19 | 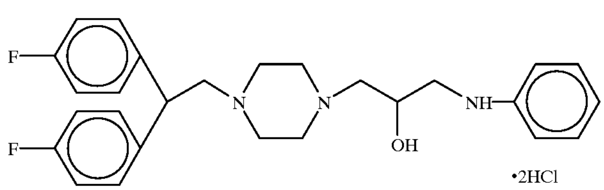 | 2 | 0 | H | H | H | H | 1-[2,2-diphenylethyl)-4-(2-hydroxy-3-phenylamino-propyl)piperazine.2HCl |

TABLE 4-continued

| PR-No. | Structure | m | n | R$_1$ | R$_2$ | R$_3$ | R$_4$ | Compound Name |
|---|---|---|---|---|---|---|---|---|
| Cpd. 20 | (structure) ·2HCl | 4 | 0 | F | F | H | H | 1-[4,4-bis(4-fluoro-phenyl)butyl]-4-[2-hydroxy-3-(4-nitrophenylamino)propyl]-piperazine.2HCl |

TABLE 5

| PR-No. | Structure | m | n | R$_1$ | R$_2$ | R$_3$ | R$_4$ | Compound Name |
|---|---|---|---|---|---|---|---|---|
| Cpd. 21 | (structure) ·2HCl | 5 | 0 | F | F | H | H | 1-[5,5-bis(4-flurophenyl)-pentyl]-4-(2-hydroxy-3-phenylaminopropyl)piperazine.2HCl |
| Cpd. 22 | (structure) ·3 CHCOOH‖CHCOOH | 4 | 0 | F | F | H | H | 1-[4,4-bis(4-flurophenyl)-butyl]-4-[3-(3,5-di-tert-butyl-4-hydroxyphenylamino)-2-hydroxypropyl]piperazine. .3C$_4$H$_4$O$_4$ |
| Cpd. 23 | (structure) ·3 CHCOOH‖CHCOOH | 4 | 0 | F | F | H | H | 1-[3-(4-aminophenylamino)-2-hydroxypropyl]-4-[4,4-bis(4-fluorophenyl)butyl]-piperazine.3C$_4$H$_4$O$_4$ |
| Cpd. 24 | (structure) ·2 CHCOOH‖CHCOOH | 4 | 0 | F | F | H | H | 1-[4,4-bis(4-flurophenyl)-butyl]-4-[3-(4-dimethyl-aminophenylamino)-2-hydroxy-propyl]piperazine.2C$_4$H$_4$O$_4$ |
| Cpd. 25 | (structure) ·2 CHCOOH‖CHCOOH | 4 | 0 | F | F | H | H | 1-[4,4-bis(4-flurophenyl)-butyl]-4-[2-hydroxy-3-(4-hydroxyphenylamino)propyl]-piperazine.2C$_4$H$_4$O$_4$ |

In the process of antagonizing narcotics, compounds (1) strongly bind to narcotic receptors so as to inhibit narcotics from binding to narcotic receptors. Needless to say, compounds (1) do not have any narcotic-like action. Therefore, compounds (1) are useful as narcotic antagonists and medicaments for the prevention and treatment of narcotic dependence. Narcotics to which the medicines of the present invention are particularly effective include cocaine, amphetamine, and phencyclidine. It is expected that the compounds are most effective on cocaine. They exhibit very strong effects on cocaine as shown in the Examples described below.

Toxicities of formula (1) compounds are very low, as described in WO92/05165, each having a LD$_{50}$ value of not less than 1,000 mg/kg in mice. Thus, the compounds are quite safe.

The medicines of the present invention contain, as their active components, compounds of formula (1) or their salts. The medicines of the invention may also contain optional components which are commonly used in formulating medicines. Examples of optional components are vehicles, bulking agents, binders, coating agents, sugar coats, stabilizers, disintegrants, colorants, lubricants, pH adjusters, solubilizers, dispersants, thickeners, isotonic agents, oils, and waxes. The medicines of the present invention are obtained by formulating one or more compounds represented by formula (1) or their salts together with pharmaceutically acceptable optional components by a routine method.

The types of the medicines of the present invention are not particularly limited so long as they are legally permitted. For example, they may take the form of ordinary or sustained-release type drugs for oral administration, transdermal drugs, nasal drugs, rectal drugs, drip infusions, or Vorus' injections of these, peroral, injection, and nasal drugs are preferred. Suitable doses vary with the characteristics of patients such as their condition, age, body type, etc. In the case of oral administration, a dose of 10–1,000 mg compound/day is preferred, whereas in the case of parenteral administration, a dose of 1–500 mg compound/day is preferred, both doses applicable to an adult. The medicines are preferably administered several times daily, thereby make it possible to retain the constant concentration of active agents in blood.

EXAMPLES

The present invention will next be described by way of examples, which should not be construed as limiting the invention.

Example 1

In vitro binding inhibition assay against a cocaine derivative

Male Wistar rats were decapitated. From each rat, striatum was immediately removed, and its wet weight was measured. The tissue of striatum was homogenized using a polytron together with a 10-fold amount of 50 mM Tris-HCl buffer (pH 7.4) while being cooled on ice. The homogenate was centrifugally separated (38,700 G, 20 minutes, 4° C.), and the resulting pellet was suspended in a mixture of a 40-fold amount (based on the original tissue weight) of 50 mM Tris-HCl and 100 mM NaCl buffer (pH 7.4).

The crude membrane sample suspended in the above-described mixture of 50 mM Tris HCl and 100 mM NaCl buffer (pH 7.4), a cocaine derivative [$^3$H]WIN35,428 (product of NEN, final concentration: 0.5 nM), and a test drug (final concentration: $1\times10^{-10}$ to $1\times10^{-5}$ M) were placed in an incubation tube. The contents were allowed to react for 2 hours on ice (0–4° C.). Reaction was terminated by passing the contents through a glass filter (GF/B, product of Whatman) which had been immersed in 0.1% BSA solution for at least 40 minutes in advance while aspiration was carried out using a cell harvester, followed by washing three times with 5 ml of 50 mM Tris HCl buffer (pH 7.4). The filter and 10 ml of aquazol 2 (product of NEN) were placed in a vial and allowed to stand overnight. Radioactivity was measured using a liquid scintillation counter. Nonspecific binding amounts were determined as the binding amounts obtained in the presence of 10 $\mu$M (final concentration) of WIN35065-2 (product of Research Biochemical International, a cocaine derivative). Specific binding amounts were determined by subtracting the nonspecific binding amounts from the total binding amounts. Fifty(50)% inhibition concentrations were calculated using Hill plotting. The results are shown in Table 6. GBR12909 (product of Research Biochemical International) which is under development as a therapeutic agent for cocaine dependence, was used as a positive control.

TABLE 6

| Compound No. | 50% Inhibition concentration (nM) |
|---|---|
| Compound 1 | 44.8 |
| Compound 2 | 51.6 |
| Compound 3 | 31.7 |
| Compound 4 | 49.5 |
| Compound 6 | 34.9 |
| Compound 7 | 41.2 |
| Compound 8 | 23.7 |
| Compound 9 | 46.8 |
| Compound 11 | 196.7 |
| Compound 13 | 105.5 |
| Compound 15 | 37.6 |
| Compound 16 | 52.6 |
| Compound 17 | 45.0 |
| Compound 18 | 15.0 |
| Compound 19 | 72.2 |
| Compound 20 | 55.8 |
| Compound 21 | 41.2 |
| Compound 22 | 306.5 |
| Compound 23 | 533.6 |
| Compound 25 | 23.7 |
| GBR12909 | 89.1 |
| WIN35,065-2 | 117.7 |
| Cocaine | 5101.7 |

From Table 6, it is found that many of compounds (1) exhibit stronger binding inhibitory action than GBR12909. Moreover, compounds (1) exhibit very strong binding inhibitory action which was not known to date. Considering that a compound of formula (1) and a cocaine derivative are in equilibrium in the test system employed and that a cocaine derivative is difficult to liberate after it is bound to a receptor, it is presumed that compound (1) cuts the linkage to a cocaine derivative and then binds itself to a receptor. In other words, the above data show that compounds (1) are useful for the treatment of patients having narcotic dependence.

Example 2

Ex vivo binding inhibition assay

To each male Wistar rat, 30 mg/kg of compound 15 was intraperitoneally administered. Thirty minutes after administration, rats were decapitated. From each rat, striatum was immediately removed, and its wet weight was measured. The tissue of striatum was homogenized using a polytron together with a 10-fold amount of 50 mM Tris-HCl buffer (pH 7.4) while being cooled on ice. The homogenate was centrifugally separated (20,000 G, 20 minutes, 4° C.), and the resulting pellet was suspended in a mixture of a 20-fold amount (based on the original tissue weight) of 50 mM Tris-HCl and 100 mM NaCl buffer (pH 7.4).

The crude membrane sample suspended in the above-described mixture of 50 mM Tris-HCl and 100 mM NaCl buffer (pH 7.4) and a cocaine derivative [$^3$H]WIN35,428 (product of NEN, final concentration: 0.5 nM) were placed in an incubation tube. The contents were allowed to react for 2 hours on ice (0–4° C.). Reaction was terminated by passing the contents through a glass filter (GF/B, product of Whatman) which had been immersed in 0.1% BSA solution for at least 40 minutes in advance while aspiration was carried out using a cell harvester, followed by washing three times with 5 ml of 50 mM Tris HCl buffer (pH 7.4). The filter and 10 ml of aquazol 2 (product of NEN) were placed in a vial and allowed to stand overnight. Radioactivity was measured using a liquid scintillation counter. Nonspecific binding amounts were determined as the binding amounts obtained in the presence of 10 μM (final concentration) of WIN35065-2 (product of Research Biochemical International, a cocaine derivative). Specific binding amounts were determined by subtracting the nonspecific binding amounts from the total binding amounts. Control accounts for the sole use of a saline solution administered to rats intraperitoneally. As a result, the binding inhibitory ratio in the control group was 0% and the ratio in the group of compound 15 was 86.1%. Thus, the compound of the present invention exhibited excellent in vivo binding inhibitory action on cocaine as was exhibited ex vivo. Moreover, in view that the compound of formula (1) was pre-administered in this experiment, it is apparent that the compound is useful as a preventive drug for narcotic dependence.

Examples 3–4

(Formulation Examples)

The following components were measured and placed in a Grad granulator and mixed at a low speed. Thereafter, a 5-fold amount of an aqueous 50% ethanol solution was sprayed portionwise thereto, and granulated at a high speed. The resulting granules were dried with air (40° C.) stream for 48 hours, and were passed through a sieve to obtain granules.

| (Components) | (parts by weight) |
|---|---|
| Crystalline cellulose | 38 |
| Lactose | 40 |
| Hydroxypropylcellulose | 10 |
| Hydrochloric acid salt of compound 1 | 10 |
| Aluminum stearate | 2 |

Example 5

(Formulation Example)

The following components were dissolved at 80° C., placed in a mold, cooled, and removed from the mold, to obtain suppositories.

| (Components) | (parts by weight) |
|---|---|
| Vaseline | 20 |
| Suppository base G | 70 |
| Compound 4 | 10 |

Example 6

(Formulation Example)

Compound 1 (1 g) was subjected to liquid-liquid extraction using an aqueous saturated sodium hydrogencarbonate solution (100 ml) and diethyl ether (100 ml). The ether layer was collected and washed with water. The solvent was evaporated to obtain compound 1 in the free state. A portion (100 mg) of the compound was measured and placed in a 20-ml aerosol container can. A nozzle was attached to the container, after which the container was sealed. Flon gas was injected into the container to obtain a nasal agent.

| (Components) | (parts by weight) |
|---|---|
| Crystalline cellulose | 38 |
| Lactose | 40 |
| Hydroxypropylcellulose | 10 |
| Oxalic acid salt of compound 2 | 5 |
| Citric acid salt of compound 3 | 5 |
| Aluminum stearate | 2 |

Example 7

(Formulation Example)

The following components were heated and kneaded with a kneader, and cooled to obtain a transnasal composition.

| (Components) | (parts by weight) |
|---|---|
| Vaseline | 80 |
| Liquid paraffin | 9 |
| Phosphatidyl choline | 1 |
| Compound 6 | 10 |

As described above, the narcosic antagonists of the present invention have potent narcotic antagonizing activities, and therefore, they are very useful in the prevention and treatment of narcotic dependence due to cocaine, for example.

What is claimed is:

1. A method for preventing or treating narcotic dependence comprising administering an effective amount of a composition to a patient in need thereof; said composition comprising an effective amount of a compound or a physiologically acceptable salt thereof, wherein said compound is selected from the group consisting of 1-[4,4-bis(4-fluorophenyl)-butyl]-4-(2-hydroxy-3-phenylaminopropyl)piperazine.2HCl, 1-[bis(4-fluorophenyl)-methyl]-4-[2-hydroxy-3-phenylaminopropyl)-piperazine.2HCl, 1-[4,4-bis(4-fluorophenyl)-butyl-]-4-(2-hydroxy-3-benzylaminopropyl)piperazine.2HCl, 1-[4,4-bis(4-fluorophenyl)-butyl-]-4-(2-methoxy-3-phenylaminopropyl)piperazine.2HCl, 1-[4,4-bis(4-fluorophenyl)-butyl-]-4-[3-(4fluorophenylamino)-2-hydroxypropyl]-piperazine.2HCl, (−)-1-[4,4-bis(4-fluorophenyl)butyl]-4-(2-hydroxy-3-phenylaminopropyl)-piperazine.2HCl, (+)-1-[4,4-bis(4-fluorophenyl)butyl]-4-(2-hydroxy-3-phenylaminopropyl)-piperazine.2HC, 1-[4,4-bis(4-fluorophenyl)butyl]-4-[2-hydroxy-3-(4-pyridylamino)propyl]-piperazine.$2C_4H_4O_4$, 1-[3,3-bis(4-fluorophenyl)-propyl]-4-[2-hydroxy-3-phenylaminopropyl)piperazine.2HCl, and 1-[5,5-bis(4-fluorophenyl)pentyl]-4-(2-hydroxy-3-phenylaminopropyl)piperazine.2HCl; and a pharmaceutically acceptable carrier.

2. The method of claim 1 wherein said compound is administered in an effective amount which does not produce adverse side effects.

3. A method as claimed in claim 2 wherein the compound is 1-[4,4-bis(4-fluorophenyl)-butyl]-4-(2-hydroxy-3-phenylaminopropyl)piperazine.2HCl.

4. A method as claimed in claim 2 wherein the compound is 1-[bis(4-fluorophenyl)-methyl]-4-[2-hydroxy-3-phenylaminopropyl)-piperazine.2HCl.

5. A method as claimed in claim 2 wherein the compound is 1-[4,4-bis(4-fluorophenyl)-butyl]-4-(2-hydroxy-3-benzylaminopropyl)piperazine.2HCl.

6. A method as claimed in claim 2 wherein the compound is 1-[4,4-bis(4-fluorophenyl)-butyl]-4-(2-methoxy-3-phenylaminopropyl)piperazine.2HCl.

7. A method as claimed in claim 2 wherein the compound is 1-[4,4-bis(4-fluorophenyl)-butyl]-4-[3-(4-fluorophenylamino)-2-hydroxypropyl]-piperazine.2HCl.

8. A method as claimed in claim 2 wherein the compound is (−)-1-[4,4-bis(4-fluorophenyl)butyl-]-4-(2-hydroxy-3-phenylaminopropyl)-piperazine.2HCl.

9. A method as claimed in claim 2 wherein the compound is (+)-1-[4,4-bis(4-fluorophenyl)butyl-]4-(2-hydroxy-3-phenylaminopropyl)-piperazine.2HCl.

10. A method as claimed in claim 2 wherein the compound is 1-[4,4-bis(4-fluorophenyl)butyl-]-4-[2-hydroxy-3-(4-pyridylamino)propyl]-piperazine.2$C_4H_4O_4$.

11. A method as claimed in claim 2 wherein the compound is 1-[3,3-bis(4-fluorophenyl)-propyl]-4-[2-hydroxy-3-phenylaminopropyl)piperazine.2HCl.

12. A method as claimed in claim 2 wherein the compound is 1-[5,5-bis(4-fluorophenyl)pentyl-]-4-(2-hydroxy-3-phenylaminopropyl)piperazine.2HCl.

13. A method as defined in claim 1 wherein the narcotic is one or more members selected from the group consisting of cocaine and/or its analogs.

\* \* \* \* \*

UNITED STATES PATENT AND TRADEMARK OFFICE
CERTIFICATE OF CORRECTION

PATENT NO. : 6,100,280
DATED : August 8, 2000
INVENTOR(S) : Inazu et al.

It is certified that error appears in the above-identified patent and that said Letters Patent is hereby corrected as shown below:

Column 14,
Line 51, please correct "2HC," to -- 2HCl, --.

Column 15,
Line 14, please correct "butyl-]-4-" to -- butyl]-4- --.

Signed and Sealed this

Fifth Day of October, 2004

JON W. DUDAS
*Director of the United States Patent and Trademark Office*